US 6,606,816 B2

(12) United States Patent
Oi et al.

(10) Patent No.: US 6,606,816 B2
(45) Date of Patent: *Aug. 19, 2003

(54) GROUND SURFACE NON-EDIBLE FORAGING MATRIX CONFIGURATIONS FOR ARTHROPOD CONTROL

(75) Inventors: Faith M. Oi, Gainesville, FL (US); Philip G. Koehler, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/097,813

(22) Filed: Mar. 13, 2002

(65) Prior Publication Data

US 2002/0157302 A1 Oct. 31, 2002

Related U.S. Application Data

(63) Continuation-in-part of application No. 09/942,341, filed on Aug. 29, 2001, and a continuation-in-part of application No. 09/525,086, filed on Mar. 14, 2000, now Pat. No. 6,298,597.
(60) Provisional application No. 60/243,905, filed on Oct. 27, 2000, and provisional application No. 60/159,266, filed on Oct. 13, 1999.

(51) Int. Cl.[7] .......................... A01M 1/20; A01M 25/00
(52) U.S. Cl. .......................... 43/131; 43/132.1; 43/107; 43/124; 43/121; 106/15.05; 424/411; 424/84
(58) Field of Search .............................. 43/131, 132.1, 43/107, 124, 121; 106/15.05; 424/411, 84

(56) References Cited

U.S. PATENT DOCUMENTS

| 1,634,648 | A | * | 7/1927 | Cardinet | |
|---|---|---|---|---|---|
| 2,931,140 | A | | 5/1960 | Laffler | 47/48.5 |
| 3,624,953 | A | * | 12/1971 | Crosby | |
| 3,835,578 | A | | 9/1974 | Basile | 43/132 |

(List continued on next page.)

FOREIGN PATENT DOCUMENTS

GB          2306886     *  5/1997    .......... A01N/25/08

OTHER PUBLICATIONS

*Laboratory Evaluation I of Insecticides for Control of Tarnished Plant Bug in Mississippi*, research report from University of Mississippi website, 1995. 2 pages (p. 1 and 2 of 3).

(List continued on next page.)

*Primary Examiner*—Charles T. Jordan
*Assistant Examiner*—Andrea M. Valenti
(74) *Attorney, Agent, or Firm*—Law Offices of Brian S. Steinberger, P.A.; Brian S. Steinberger

(57) ABSTRACT

Surface ground kits for controlling arthropods such as termites, carpenter ants, fire ants, roaches, and the like, and combinations thereof. Embodiments can include mounting a chamber on a ground insertable member having an edible food source, such as a wood stake, and pressing the member into the ground until the chamber is against the ground surface. The chamber can be cylindrical disc shape having one closed end and closed sides, such as plastic cup, Petri dish, and the like. Optionally, the chamber can be non-opaque so that the interior contents can be viewed from outside the chamber. The lower open end of the chamber can be a layer of an edible non-toxic material such as a layer of foam, and the like. On top of the edible layer, can be a layer of a non-edible foraging matrix that contains the slow-acting non-repellent toxicant within the foraging matrix, and this layer can be visible through the top closed portion of the chamber. Arthropods can be attracted to the kit device by the edible portion of the ground insertable member. The arthropods can then pass through the edible foam type layer in the open end of the chamber and then forage into the layer containing the non-edible material which is mixed with the slow-acting non-repellent toxicants. The arthropods leave the chamber in the same direction they came taking the slow-acting non-repellent toxicant back to their galleries and colonies where the arthropods are killed over time. Ground engaging members such as stake(s) and/or teeth and/or lower extending edges can also be used. Removable lid portions such as snap tops, screwable threads, and hinged tops can allow the chambers to be monitored and/or reusuable overtime.

34 Claims, 13 Drawing Sheets

U.S. PATENT DOCUMENTS

| | | | | |
|---|---|---|---|---|
| 3,940,875 A | | 3/1976 | Basile | 43/124 |
| 4,043,073 A | | 8/1977 | Basile | 43/124 |
| 4,709,503 A | * | 12/1987 | McQueen | 43/114 |
| 5,435,096 A | | 7/1995 | Nekomoto | 43/112 |
| 5,528,854 A | * | 6/1996 | Antonali et al. | 43/131 |
| 5,555,672 A | * | 9/1996 | Thorne et al. | 43/124 |
| 5,592,774 A | | 1/1997 | Galyon | 43/124 |
| 5,746,021 A | * | 5/1998 | Green | 43/131 |
| 5,778,596 A | | 7/1998 | Henderson et al. | 43/132.1 |
| 5,815,090 A | | 9/1998 | Su | 340/870.16 |
| 5,832,658 A | * | 11/1998 | Randon | 43/131 |
| 5,918,410 A | * | 7/1999 | Knuppel | 43/131 |
| 5,921,018 A | * | 7/1999 | Hirose et al. | 43/132.1 |
| 5,927,000 A | * | 7/1999 | Bordes, Jr. | 43/124 |
| 5,935,943 A | | 8/1999 | Asai et al. | 514/63 |
| 5,950,356 A | * | 9/1999 | Nimocks | 43/131 |
| 5,979,108 A | * | 11/1999 | Adams | 43/121 |
| 6,014,834 A | * | 1/2000 | Ferland | 43/131 |
| 6,016,625 A | * | 1/2000 | Bishoff et al. | 43/121 |
| 6,052,066 A | | 4/2000 | Su | 340/870.16 |
| 6,058,646 A | * | 5/2000 | Bishoff et al. | 43/131 |
| 6,079,150 A | | 6/2000 | Setikas et al. | 43/132.1 |
| 6,178,834 B1 | * | 1/2001 | Cates | 73/865.8 |
| 6,187,328 B1 | * | 2/2001 | Ballard et al. | 424/409 |
| 6,195,934 B1 | * | 3/2001 | Megargle et al. | 43/131 |
| 6,219,960 B1 | * | 4/2001 | Contadini et al. | 43/121 |
| 6,219,961 B1 | * | 4/2001 | Ballard et al. | 43/131 |
| 6,235,301 B1 | * | 5/2001 | Ballard et al. | 424/405 |
| 6,272,791 B1 | | 8/2001 | Pleasants | 43/131 |
| 6,298,597 B1 | * | 10/2001 | Koehler et al. | 43/131 |
| 6,370,812 B1 | | 4/2002 | Burns et al. | 43/124 |
| 6,397,516 B1 | | 6/2002 | Su | 43/124 |

OTHER PUBLICATIONS

*Letter to Kandy Walker Duke at Rhone Merieux from New York State Department of Environmental Conservation*, letter dated Feb. 7, 1997, obtained from website address: pmep.cce.cornell.edu, updated Dec. 16, 1007. 2 pages (p. 1 & 2 of 3).

*Rhône–Poulec's Fipronil give approval for Clorox Products*, press release from library section of website www.rhone–poulec.com, Aug. 5, 1997, last updated Feb. 11, 1998. 1 page.

*Toxicity and Degradation of Fipronil Applied to Cotton for control of Boll Weevils*, Joseph E. Mulrooney and Deepa Goli, interpretive summary for TEKTRAN website address www.nal.usda.gov, Dec. 3, 1997. p. 1 of 2.

*Fiproil*, NPTN fact sheet on Fipronil from National Pesticide Telecommunicatioins Network website, 5 pages, Dec. 1997.

*Prospective Study Comparing Fipronil with dichlorvas/fenitrothion and methoprene/pyrethrins in control of Flea Bite Hypersensitivity in Cats*, R.G. Harvey, E.J. Penaliggon, and P. Gautier, Veterinary Record (1997), www.inno–vet.com. p. 1.

Website www.peteducation.com, general information on Fipronil as used in flea prevention and treatment 1997, 3 pages.

*Control of Corn Root Worm in Green Peas*, WSU cooperative extension research report. Washington State University, www.agsyst.wsu.edu, last updated Jul. 24, 2000, p. 1 to 5.

*Residue Analysis of Fipronil and its Metabolites Observec in Leek Samples*, Guido Goller, Patrick Duchene and Marc Maestracci, report available on website www.chemsoc.org, no date listed, one page.

*Evaluation of Fipronil for residual control of mole crickets on turfgrass*, Table of results using Fipronil to treat mole crickets on turfgrass, no date listed, one page.

*Field Trials to Evaluate the Efficacy of Fipronil (regent R) for Controlling Rice Insects Under Different Formulations*, Luuong Minh Chau, report posted on website www.chemsoc.org, no date listed, two pages.

*Maxforce Bait Gel–FC–German Roaches*, www.roachcontrol.com, website advertisement for Maxforce Gel FC, no date listed, three pages.

* cited by examiner

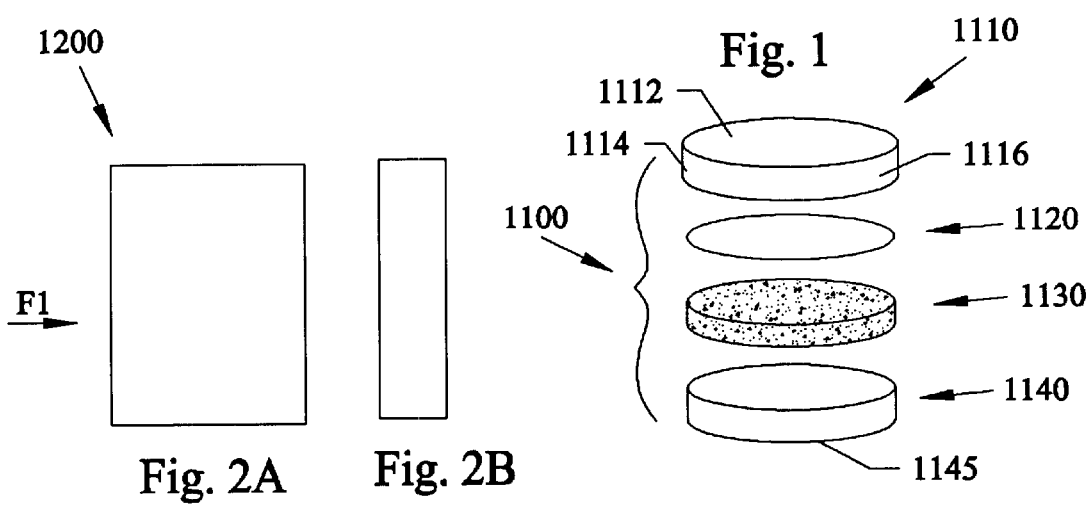
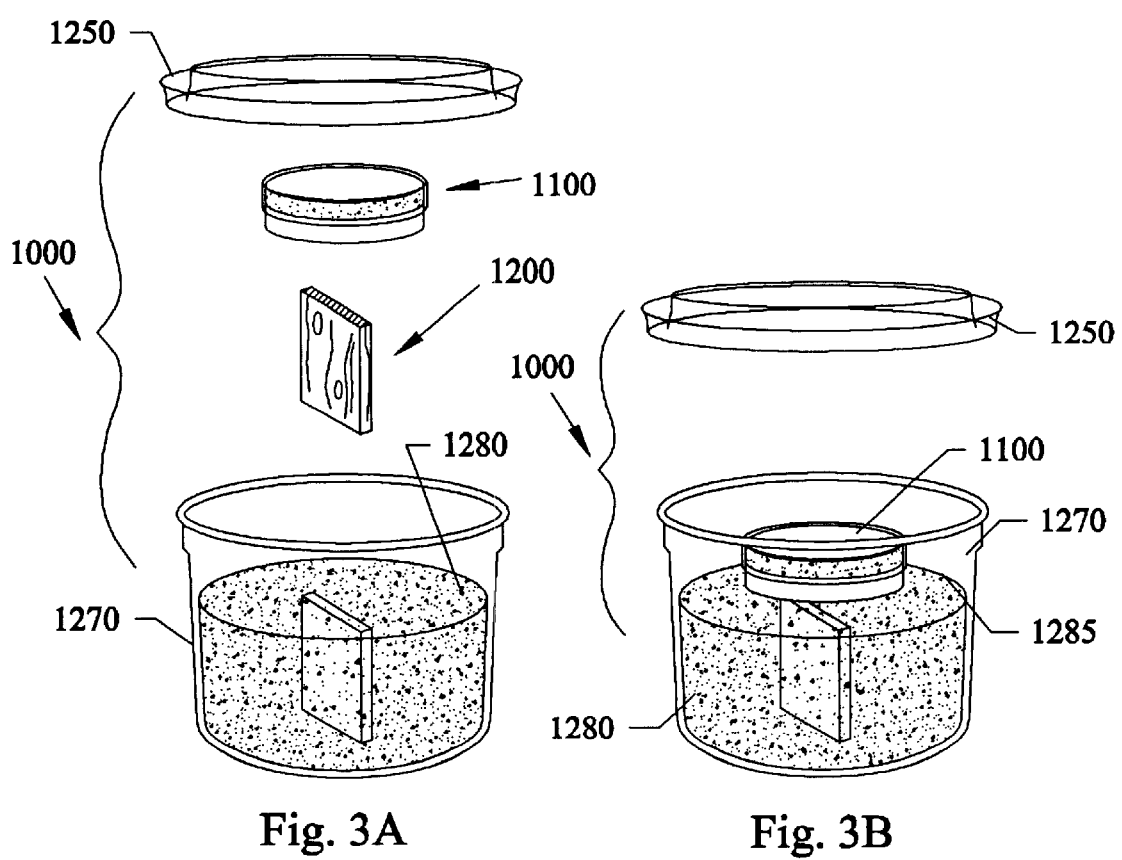

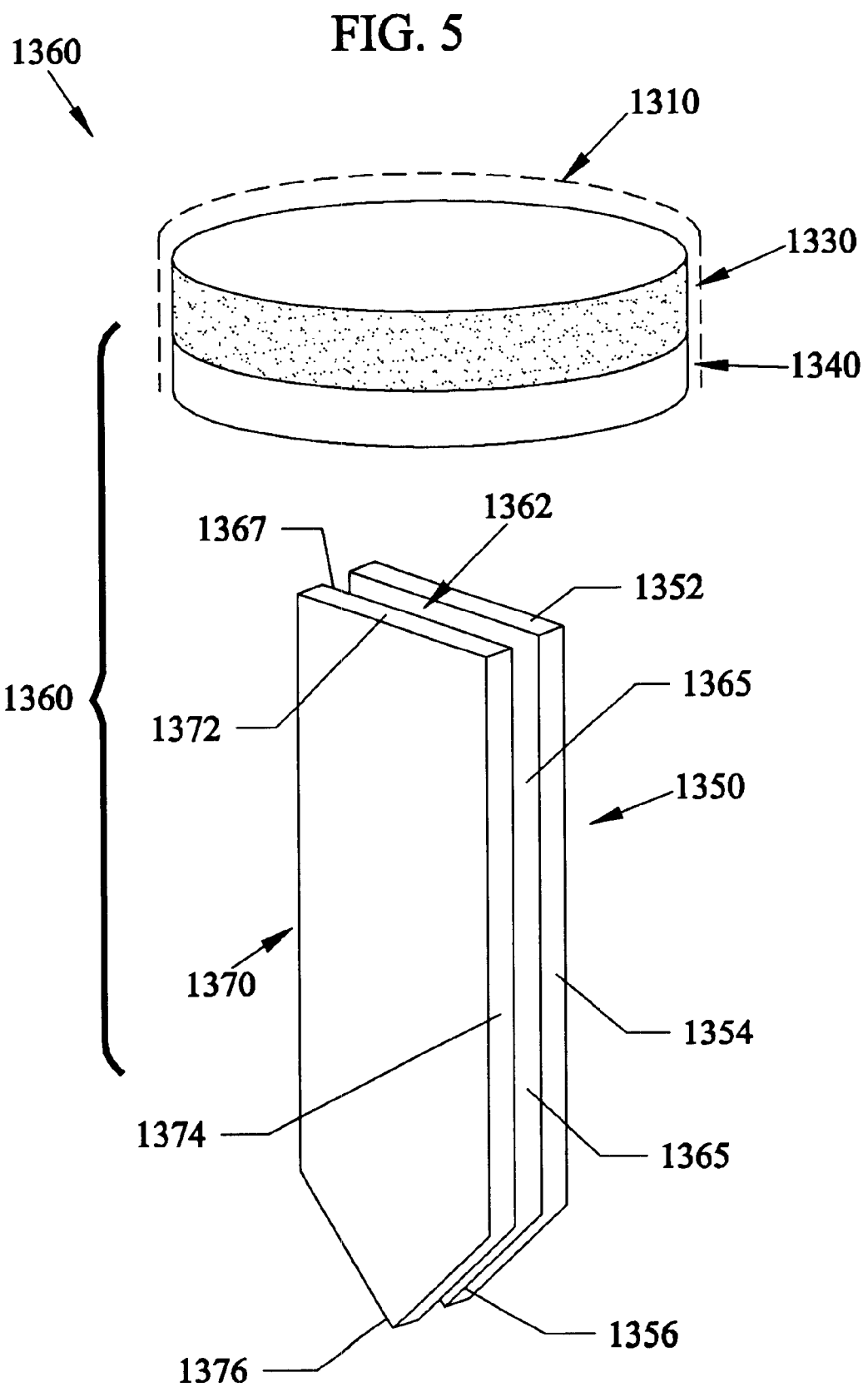

GROUND SURFACE NON-EDIBLE FORAGING MATRIX CONFIGURATIONS FOR ARTHROPOD CONTROL

This invention relates to ground surface controls for arthropods such as termites, carpenter ants, fire ants and roaches, and in particular to apparatus and methods for using a non-toxic food source to attract the arthropods into housings having a non-edible foraging matrix treated with slow acting and non-repellant toxicants, that causes the arthropods to take the toxicants back to galleries and living areas in their colonies, and this invention is a Continuation-In-Part of U.S. application Ser. No. 09/942,341 filed Aug. 29, 2001, which claims the benefit of priority to U.S. Provisional Application No. 60/243,905 filed Oct. 27, 2000, by the same inventors and assignee as the subject invention, and which also is a Continuation-In-Part of U.S. application Ser. No. 09/525,086 filed Mar. 14, 2000 by the same inventors and a co-assignee of the subject invention which is now U.S. Pat. No. 6,298,597, and which claims the benefit of priority to U.S. Provisional Application No. 60/159,266 filed Oct. 13, 1999.

BACKGROUND AND PRIOR ART

Common nuisance pests that are of a primary concern for causing damage generally include arthropods such as termites, carpenter ants, fire ants and roaches. In southern areas especially Florida, termites are considered to be one of the most destructive arthropod pests for any manmade structures containing wood such as the framing in homes, as well as for causing destruction to natural wood containing items such as trees, and the like.

The two forms of termites that are of concern for pest control are subterranean termites and dry wood termites. Subterranean termites typically nest in the ground and usually maintain some sort of ground connection at all times. Dry wood termites usually start off in damaging pieces of wood materials, and do not require a ground connection. Between the two forms, the subterranean termites are the most damaging type of termites and usually enter structures such as buildings from surround soil adjacent to the structures.

Over the years there have been at least several methods of subterranean termite control. For example, the most common method of subterranean termite control requires soil underlying a structure to be treated with a termiticide barrier to prevent the termites from entering the structure from the ground. For example, a typical structure such as a house would have used hundreds of gallons of termiticide that would have been used to treat the soil underneath the house foundation.

From approximately 1950 to approximately 1988, a popular method for barrier treatment control for subterranean termites was chlorinated hydrocarbons. However, environmental concerns with those chemical treatments resulted in problems with the soil that could last up to approximately 35 years. Replacement chemicals for the chlorinated hydrocarbons were not popular since the replacement chemicals had a high rate of failure which resulted in extensive termite damage to the structures.

Problems with the barrier treatments became further compounded since builders have often been known to dump substantial amounts of termite edible building materials, such as wood and cardboard scraps, into the underlying soil that have served as guide lines for allowing the termites to then enter from the soil up and into the structures. These edible debris are a substantial food source, that increases the likelihood of termite infestation into the structure.

Over the years, different techniques have been developed and proposed to enhance the underground delivery of toxic insecticides beneath structures. See for example, U.S. Pat. Nos. 3,940,875 and 4,043,073 to Basile; and U.S. Pat. No. 4,625,474 to Peacock. However, many of these techniques and systems such as Basile '073 are concerned with trying to refresh the initial termiticide barrier by having the termites chew through a container with the toxicant (for example). Other examples of these techniques and systems allow for installing a piping system during the building construction process so that additional termiticide can be pumped under a slab of the building at intervals during construction. Furthermore, some of these techniques and systems such as the Basile '073 patent utilized a toxicant (for example, dieldrin) which has been banned by the EPA (Environmental Protection Agency) for termite treatment. Additionally, the pipes used in the pumping delivery systems have been known to often get clogged after installation making the pipe delivery systems not reliable nor usable overtime.

Other well-known subterranean termite treatment techniques and systems include bait techniques, which require termites to forage into a monitor that contains a non-toxic food source. Once termites infest the non-toxic food source, a food source laced with a toxicant (toxic bait) is replaced into the monitor. Termites continue to be recruited into the monitor and feed on the toxic bait. Consumption and trophallaxis (feeding other termites) of the toxic bait later causes many termites to die. See for example, U.S. Pat. No. 5,329,726 to Thome et al.; U.S. Pat. No. 5,899,018 to Gordon et al.; and U.S. Pat. No. 5,950,356 to Nimocks. However, these techniques generally require that the termites consume the toxic bait. Termites refuse to consume most toxicants. Therefore this technique is generally useful for only some 2 to 3 toxicants currently known in the world. Termites also refuse to consume bait food sources that are contaminated with molds or food sources that are too wet. These bait techniques do not use a non-edible foraging matrix (as described in the subject invention), such as but not limited to soil and sand, to cause the termites to tunnel therethrough and carry the non-edible particles treated with the toxicants to the galleries and living spaces of the colony, and thus contaminating the colonies. Most toxicants applied to non-edible foraging matrixes, except repellant pyrethroids, will be picked up and carried by the termites to other areas of their tunnel systems.

Other systems have been proposed but still fail to overcome the problems with the methods and applications described above. U.S. Pat. No. 3,972,993 to Kobayashi et al. requires a membrane be treated with a substance attractive to termites (due to the termite's innate searching and feeding behavior, termites are not attracted to food from a distance when allowed to forage without interference) so that when the termites chew through the membrane a toxic surface is contacted. U.S. Pat. No. 5,501,033 to Wefler delivers a liquid toxic food source for social insects such as yellow jackets and has very little use for termites. U.S. Pat. No. 5,609,879 to Myles requires the laborious harvesting of termites from the ground, sponging on an insecticidal epoxy, and returning it to the soil. U.S. Pat. No. 5,778,596 to Henderson et al. is a device for delivering toxic food for termites to consume. And U.S. Pat. No. 5,921,018 to Hirose provides foraging guidelines for termites to follow so the termites enter a device that captures and kills them.

There are additional problems with prior art treatments that use repellent liquids, non-repellent liquids, and baits.

When using repellent liquids, the liquid barriers need to be applied in a perfectly continuous fashion. If gaps in the treatment exist, especially with repellent termiticides, such as those belonging to the pyrethroid class, the termites will forage and find the gaps in the treatment, increasing the probability of infesting the structure.

In non-repellent liquid treatments, the termites are not able to detect that they are in a treated area; hence the classification "non-repellent", and the termites die. A major drawback for non-repellent liquid treatments is that liquid termiticides in this class are still so new that there are questions about how long they will last in the soil, especially when exposed to sun and weather. The subject invention protects the foraging matrix from the sun and weather conditions in order to prolong its' usability, and the foraging matrix can be continuously replaced as necessary to recharge the system. The application of liquid termiticide barriers requires several hundred gallons of insecticide that is pumped under structures, such as houses, and can sometimes result in the contamination of the house interior, as well as water supply wells. Most homeowners have been known to want termicide applications that are less intrusive and disruptive.

Bait type station techniques and systems are again not practical since the bait stations require a food source that is palatable to termites. Selecting the appropriate food source can be difficult. While wood is a known food source, wood is very inconsistent in composition, so manufacturers don't like to use it with toxicants.

Other known food sources such as paper food sources have other problems. For example, if paper is not packed tightly enough, it will be emptied by termites and not be able to deliver enough toxicants to kill large numbers of termites. Most cellulose material will rot when placed in the soil. Once the cellulose material food source goes bad, termites will not feed, rendering the bait ineffective.

The subject invention uses a non-edible foraging matrix treated with a slow-acting non-repellent toxicant. Termites can put the particles of the treated matrix into their mouths when they tunnel through it, and many toxicants will work because they do not need to consume it and feed it to others. The particles are returned to the colony and incorporated into their tunnels. Termites that contact the particles die several days after the toxicant on the matrix particles are contacted. The behavior of the termites moves the treated foraging matrix from the exit and entrance opening of the device's chamber to contaminate their colony and tunnels.

SUMMARY OF THE INVENTION

A primary objective of the invention is to provide a ground surface method and system for killing arthropods such as termites, carpenter ants, fire ants and roaches over time.

A secondary objective of the invention is to provide a ground surface method and system for protecting structures such as homes and buildings from destructive arthropods such as termites, carpenter ants, fire ants and roaches.

A third objective of the invention is to provide a ground surface method and system for using a non-toxic and edible food source to attract arthropods such as termites, carpenter ants, fire ants, and roaches, and causing the arthropods to then tunnel through non-edible particles that are treated with a slow-acting and non-repellent toxicant so that arthropods returning to their colonies will contaminate their galleries and living spaces with the toxicant.

A fourth objective of the invention is to provide a ground surface method and system for using non-edible particles such as soil particles, sand particles, sand particles, and the like, and mixtures thereof for dispersing toxicants to arthropods such as termites, carpenter ants, fire ants and roaches that pass through tunnels, galleries and living spaces.

A fifth objective of the invention is to provide systems and methods for treating arthropods such as termites, carpenter ants, fire ants, and roaches, that is mounted on a ground surface.

A sixth objective of the invention is to provide methods and systems for easily accessing arthropod controls without having to remove the controls from the ground.

Ground surface methods and systems are included for killing arthropods such as termites, carpenter ants, fire ants, and roaches, to protect structures such as homes and buildings. One embodiment of the ground surface method and system can include positioning the ground surface embodiment against a ground surface by having pushing a stake that protruded from underneath a chamber into the ground until a bottom portion of the chamber is adjacent to the ground surface. Inside the chamber is an open bottom end with an edible non-toxic food source such as foam which can be jammed into the open bottom end of the chamber. Above the food source can be a foraging matrix having a non-edible foraging material mixed with a slow-acting non-repellent toxicant. Additionally, the upper end of the stake can be pushed into the foam material.

Another ground surface embodiment can include longer extending sides on the chamber for penetrating into the ground until the edible non-toxic layer is located adjacent to the ground surface. Other embodiments can use plural stakes, and/or teeth members for ground engaging purposes.

Additional embodiments can include removable caps that can be either screwed on, snapped, on, or hingedly attached to the top of the chamber to allow the contents of the chamber to be replenished without having to remove the entire assembly from the ground surface.

Further objects and advantages of this invention will be apparent from the following detailed description of a presently preferred embodiment which is illustrated schematically in the accompanying drawings.

BRIEF DESCRIPTION OF THE FIGURES

FIG. 1 is an exploded view of a first ground surface embodiment of the invention showing a chamber for an arthropod control application.

FIG. 2A is a front/back view of a ground insertable stake for use with the chamber of the embodiment of FIG. 1.

FIG. 2B is a side view of the stake of FIG. 2A along arrow F1.

FIG. 3A is an exploded view of the chamber of FIG. 1 and stakes of FIGS. 2A–2B with soil.

FIG. 3B is another view of FIG. 3A with chamber attached to stake, with stake in soil.

FIG. 5 is an exploded view of a second preferred ground surface embodiment.

DESCRIPTION OF THE PREFERRED EMBODIMENT

Figure 4A:
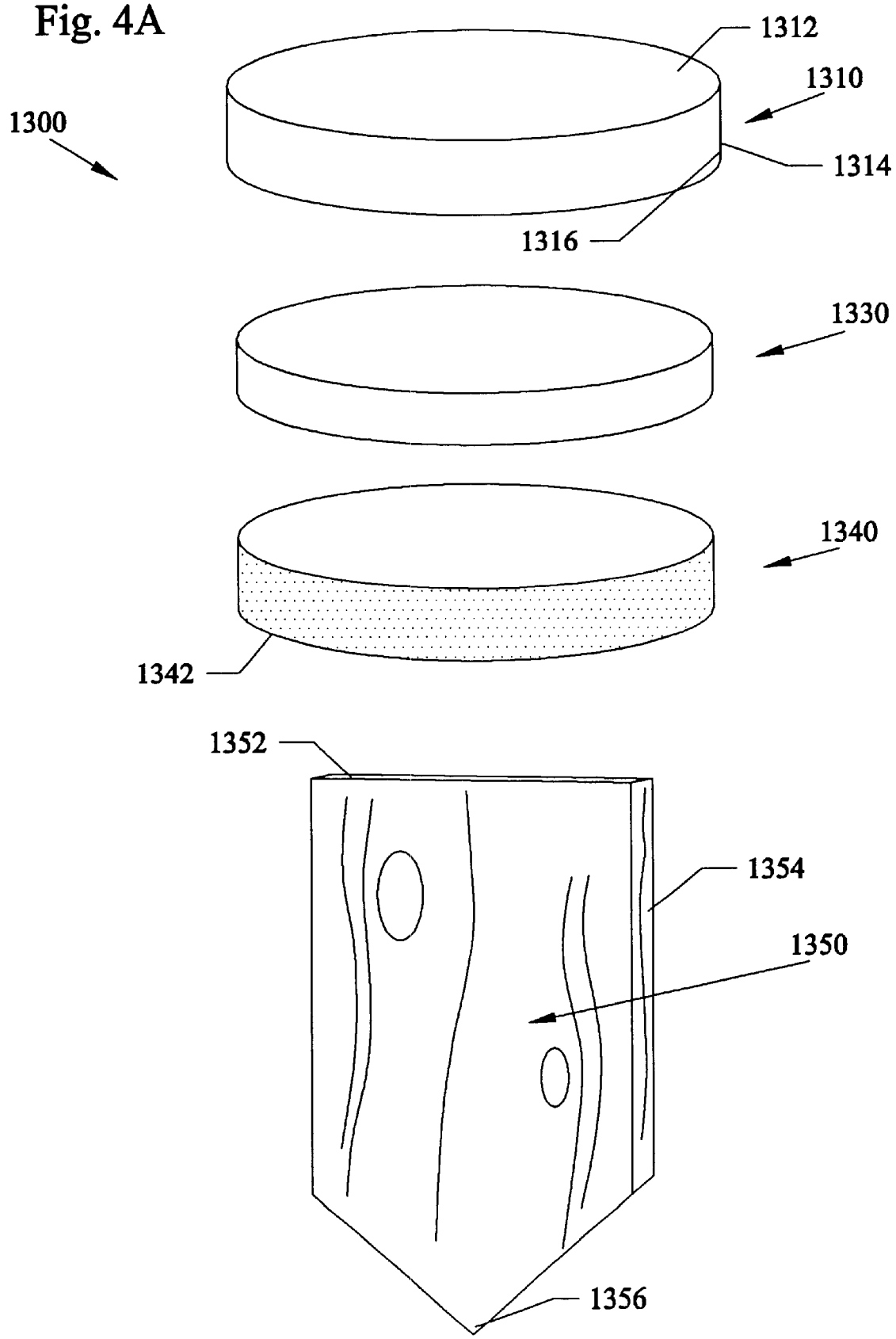
FIG. 4A is an exploded view of a preferred ground surface embodiment with sharpened stake for an arthropod control application.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Below ground embodiments for arthropod control are described in detail in the parent application Ser. No. 09/525,086 filed Mar. 14, 2000 by the same inventors and a co-assignee as that of the subject invention, now issued as U.S. Pat. No. 6,298,597, which subject matter is now incorporated by reference.

Further below ground embodiments for arthropod control are also described in detail in parent application Ser. No. 09/942,341 filed Aug. 29, 2001 to the same inventors and assignee as that of the subject invention, the subject matter of which is also incorporated by reference.

First Embodiment

FIG. 1 is an exploded view of a first ground surfaced engaging embodiment of the invention showing a chamber 1100 for a ground surface application. FIG. 2A is a front/back view of a ground insertable stake 1200 for use with the chamber 1100 of the first embodiment of FIG. 2. FIG. 2B is a side view of the stake 1200 of FIG. 2A along arrow F1. FIG. 3A is an exploded view 1000 of the chamber 1100 of FIG. 1 and stake 1200 of FIGS. 2A–2B with soil 1280 and test storage container 1270 with container lid 1250. FIG. 3B is another view of FIG. 3A with chamber 1100 attached to stake 1200, with stake 1200 in soil 1280 within container 1270.

Referring to FIGS. 1, 2A–2B and 3A–3B, chamber 1100 can include a cylindrical chamber 1110 such as a plastic see-through cylindrical disc, a petri dish, and the like, having a closed top 1112 with a diameter of approximately 5 cm, closed sides 1114 having a depth of approximately 1.3 cm and open bottom 1116. Within the open end 1116 can be an edible food surface layer 1120 such as cellulose(for example, a paper towel, and the like, can be used). Chamber 1110 can also include a non-edible foraging matrix 1130 treated with a slow-acting non-repellent toxicant having a depth of approximately. 7 cm, and closing off the open end 1116 of the chamber 1110 can be an edible non-toxic material 1140 such as foam, and the like. A stake material such as a piece of wood, and the like, 1200 can have a rectangular shape having a height of approximately 5 cm, a width of approximately 3.7 cm, and a thickness of approximately 1.3 cm. The stake 1200 can have one end that can be pressed into a side of the foam type material 1140. Next, the chamber 1110 with attached stake 1200 can be pressed into the soil 1280 within container 1270 until the lower surface 1145 of the edible non-toxic material 1140 is adjacent to the ground surface 1285.

For the invention, the slow-acting non-repellant toxicant can include but not be limited to chlorfenapyr, Fipronil, thiomethoxam, imidacloprid, hydramethylnon, sulfuramid, IGRs such as but limited to Hexaflumuron, lurfenuron, diflubenuron, and the like. The slow-acting non-repellant toxicants can be intermixed with any non-edible foraging matrix such as but not limited to builder's sand, Alachua Fine Soil, and the like, as described in the parent applications to the subject inventions which are incorporated by reference here.

Table 1 shows two trials, each having five test samples using Chlorfenapyr as the slow-acting non-repellant toxicant interspersed with the non-edible foraging matrix, compared to a untreated control samples that do not have any slow-acting non-repellant toxicants.

TABLE 1

| Treatment | Rep | Soil and Paper Towel Remaining | Ave. | Live Termites | Ave. |
|---|---|---|---|---|---|
| | | Stake with Paper #1 Chlorfenapyr 12.5 ppm Start: Oct. 22, 2001 End: Nov. 27, 2001 500 worker termites | | | |
| Chlorfenapyr 12.5 ppm | 1 | 14.3028 | 14.29728 | 0 | 0 |
| Chlorfenapyr 12.5 ppm | 2 | 13.9077 | | 0 | |
| Chlorfenapyr 12.5 ppm | 3 | 15.0171 | | 0 | |
| Chlorfenapyr 12.5 ppm | 4 | 14.5821 | | 0 | |
| Chlorfenapyr 12.5 ppm | 5 | 13.6767 | | 0 | |
| Control | 1 | 8.9579 | 9.90508 | 352 | 341.2 |
| Control | 2 | 10.223 | | 336 | |
| Control | 3 | 9.0239 | | 346 | |
| Control | 4 | 11.1471 | | 318 | |
| Control | 5 | 10.1735 | | 354 | |

TABLE 1-continued

| Treatment | Rep | Soil and Paper Towel Remaining | Ave. | Live Termites | Ave. |
|---|---|---|---|---|---|
| | | Stake with Paper #2 Chlorfenapyr 12.5 ppm Start: Dec. 12, 2001 End: Jan. 10, 2002 500 worker termites | | | |
| Chlorfenapyr 12.5 ppm | 1 | 14.7197 | 14.93606 | 0 | 0 |
| Chlorfenapyr 12.5 ppm | 2 | 14.5929 | | 0 | |
| Chlorfenapyr 12.5 ppm | 3 | 15.6261 | | 0 | |
| Chlorfenapyr 12.5 ppm | 4 | 16.2237 | | 0 | |
| Chlorfenapyr 12.5 ppm | 5 | 13.5179 | | 0 | |
| Control | 1 | . | . | 332 | 323.2 |
| Control | 2 | 10.2631 | | 324 | |
| Control | 3 | . | | 334 | |
| Control | 4 | . | | 320 | |
| Control | 5 | . | | 306 | |

Referring to Table 1, the stake test applications were placed inside a plastic deli cup with moistened sand and 500 worker termites. A petri dish with approximately 12.5 ppm chlorfenapyr treated soil was placed on top of the stake and the termites were allowed to feed and forage for approximately one month. At the end of one month, the whole apparatus was disassembled. Surviving termites were counted and the dry weight of soil and paper towel remaining in the treatment chamber were weighed. In both trials, 100% of the termites exposed to chlorfenapyr at approximately 12.5 ppm were dead, while and average of 332 termites (66.4%) survived in the untreated controls. These data clearly demonstrate that the above ground surface embodiment is an effective delivery mechanism of non-repellent toxicants.

Figure 4B:
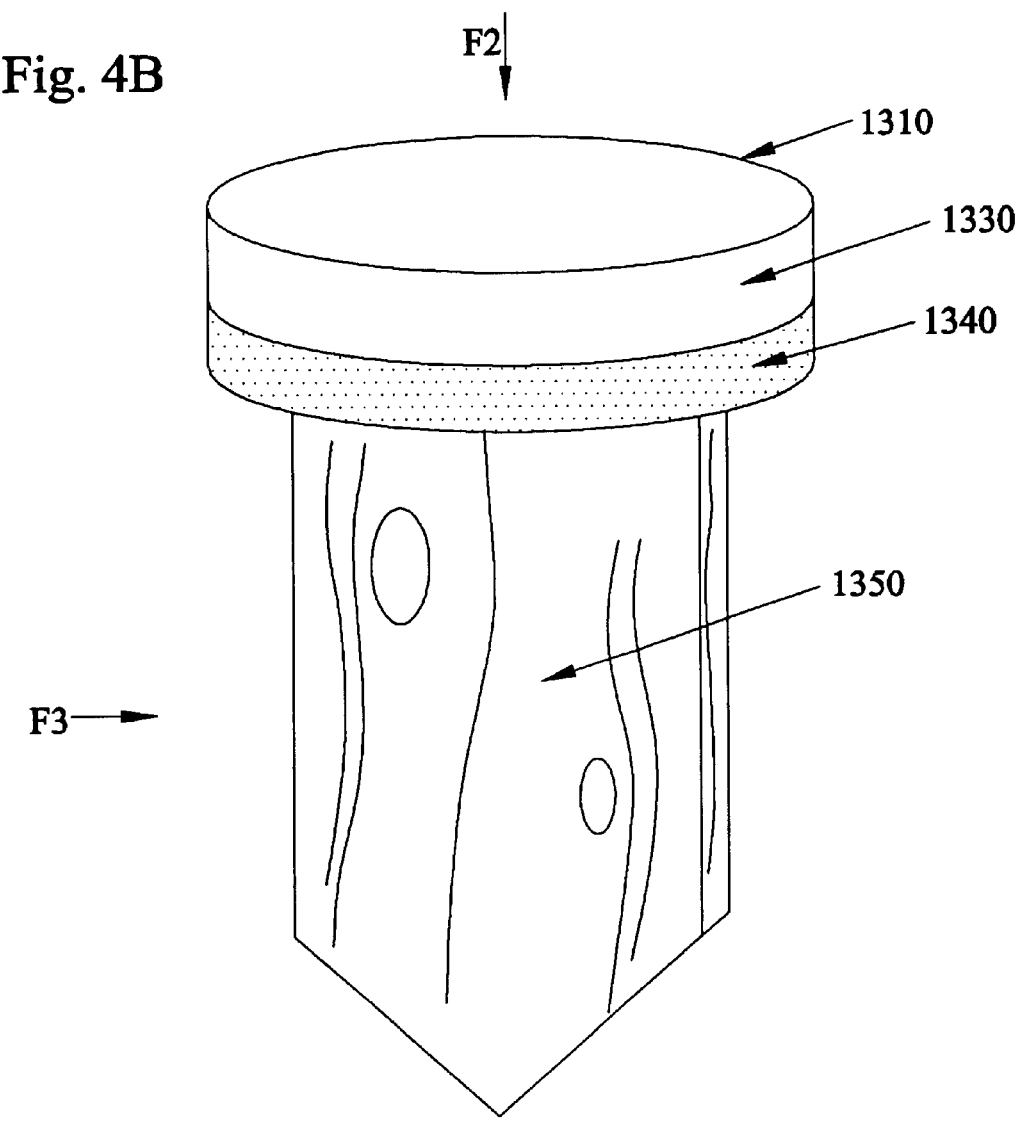
FIG. 4B is an assembled view of the preferred embodiment of FIG. 4A.
Figure 4C:
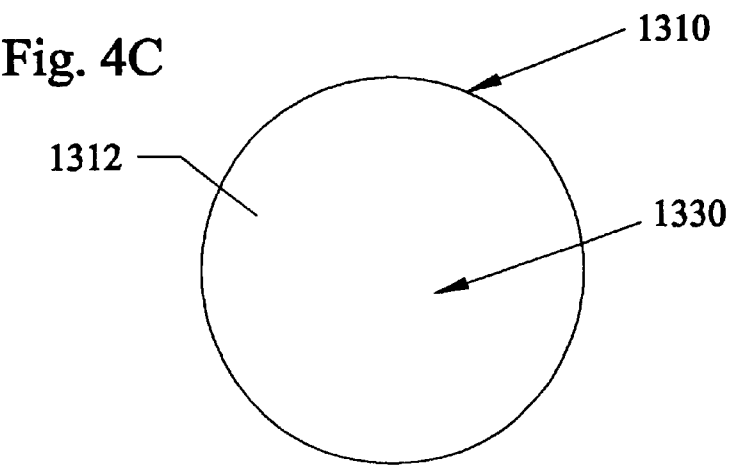
FIG. 4C is a top view of the preferred embodiment of FIG. 4B along arrow F2.
Figure 4D:
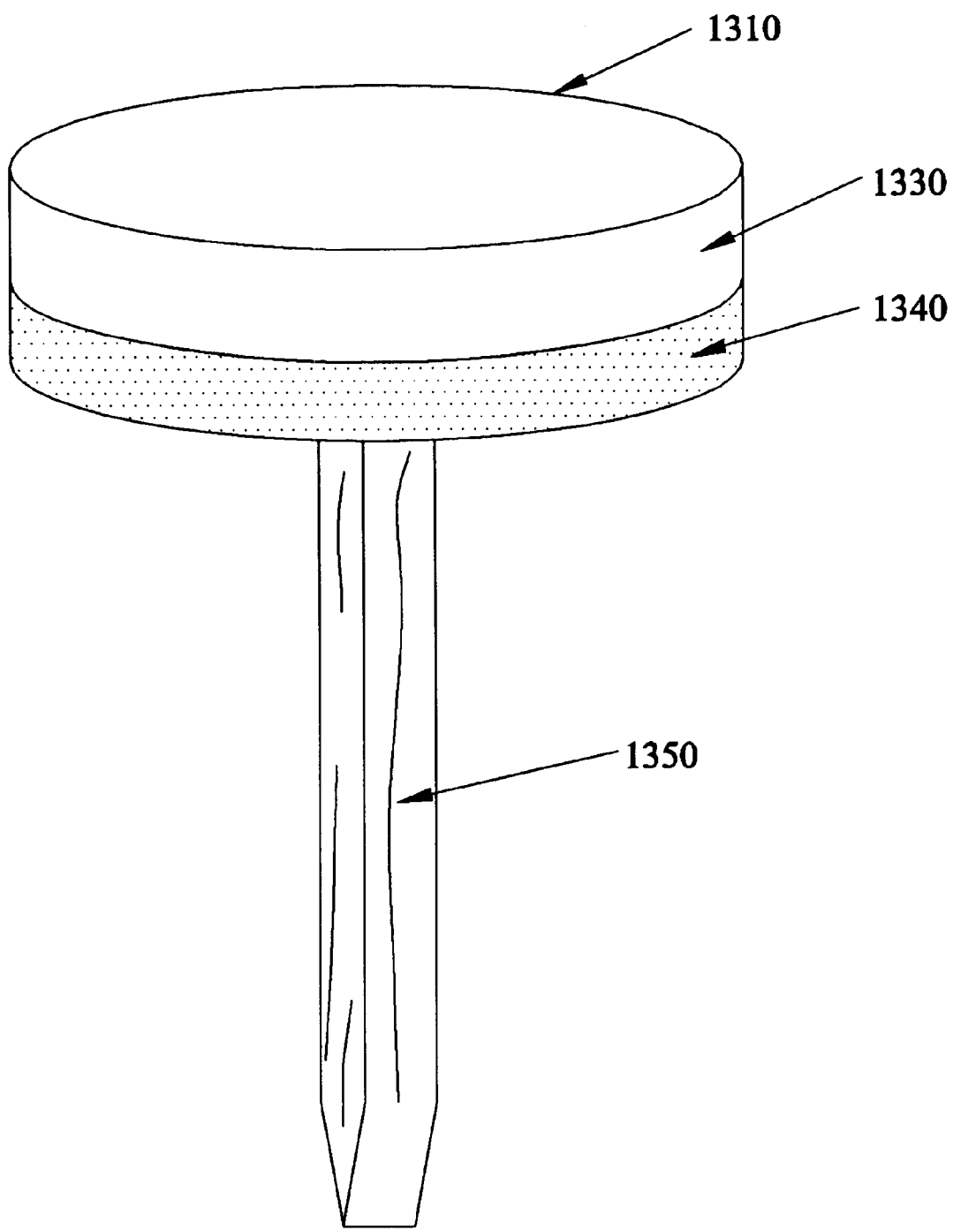
FIG. 4D is a side view of the preferred embodiment of FIG. 4B along arrow F3.

FIG. 4A is an exploded view of a preferred embodiment 1300 with sharpened stake 1350 using the invention depicted in the preceding figures. FIG. 4B is an assembled view of the preferred embodiment 1300 of FIG. 19A. FIG. 4C is a top view of the preferred embodiment 1300 of FIG. 4B along arrow F2. FIG. 4D is a side view of the preferred embodiment 1300 of FIG. 19B along arrow F3.

Referring to FIGS. 4A–4D, a preferred embodiment can include a cylindrical chamber 1310 such as a plastic see-through cylindrical disc, a petri dish, and the like, having a closed top 1312 can include a diameter of approximately 5 cm, closed sides 1314 having a depth of approximately 1.3 cm and open bottom 1316. Within the open end 1316, can be a non-edible foraging matrix layer 1310 treated with a slow-acting non-repellent toxicant having a depth of approximately. 7 cm, and closing off the open end 1116 of the chamber 1110 can be an edible non-toxic material 1340 such as foam, and the like. A stake material 1350 such as a piece of wood, and the like, can have a rectangular upper shape 1354 having a width of approximately 3.70 cm with triangular spike tipped bottom 1256, where the overall height of the stake 1350 can be approximately 5.08 cm, and a thickness of approximately 0.5 cm. The stake 1350 can have end 1352 that can be pressed into the lower exposed side 1342 of the foam type material 1340.

When used, the tip end 1356 of stake 1350 can be pressed into the ground surface until bottom end 1342 of the edible non-toxic material 1340 is adjacent to the ground surface. Arthropods can enter the chamber 1310 by following the route determined by the edible non-toxic material of the stake 1350 into the chamber, where the arthropods can forage through the non-edible foraging matrix 1330 that is treated with the slow-acting non-repellent toxicant. Arthropods leave out the same way as they entered taking the slow-acting non-repellent toxicant back to their galleries and colonies where the arthropods are killed over time. The upper closed end 1312 and/or all of the sides 1330 of the chamber 1330 can be non-opaque to allow the interior contents to be visible so that users can see the activity within the chamber 1310. See-through sides and/or top can allow users to remove and replace the embodiment overtime.

Additionally, the stake itself can be composed of a non-edible material such as metal, aluminum, and the like, to be inserted into the edible non-toxic food source layer existing in the chamber. Additionally, the stake can have longitudinal grooves down its side(s) which can also allow termites to more easily move into the chamber.

Second Embodiment

FIG. 5 is an exploded view of a second preferred ground surface embodiment 1360. FIG. 5 can include the same components as that of FIGS. 4A–4D with the addition of a second stake 1370 spaced close to and apart from first stake 1350. Second stake 1370 has top portion 1372, side edges 1374 and bottom tip 1376 which correspond to similar numbers 1352, 1354, 1356 of the first stake 1350. A spacer 1362 can keep the stakes apart from one another so that grooved passageways 1365, 1367 along either or both sides of the stakes 1350, 1370 exist, which can allow the termites a direct path to move into the chamber 1310 as previously described.

Figure 6:
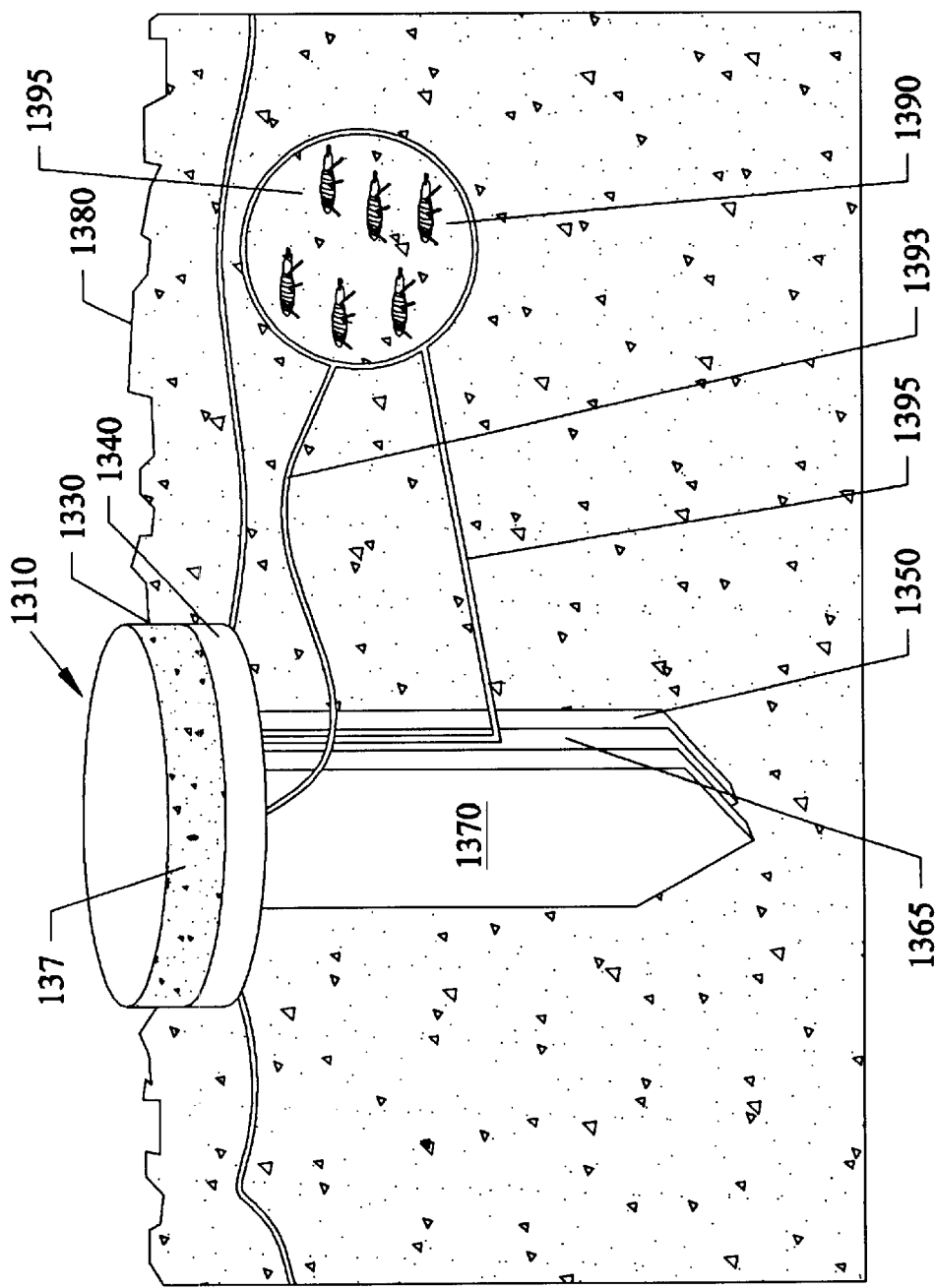
FIG. 6 shows a view of the second preferred embodiment of FIG. 5 in a ground surface application.

FIG. 6 shows a view of the second preferred embodiment of FIG. 5 in a ground surface application. Here, embodiment 1360 is placed so that stakes 1350, 1370 are pushed into the ground 1380 so that upper compartment 1310 housing the layers 1330, 1340 are adjacent to the ground surface. Arthropods such as termites 1395 in colonies, and the like, can path through tunnels 1393, 1395 to layer 1340, directly 1393, and/or by passing through groove(s) 1365 in the sides of stakes 1350, 1370. As previously described, the termites 1395 can bring back the slow-acting non-repellant toxicants to their colonies and tunnels which can kill the arthropods over time.

Third Embodiment

Figure 7:
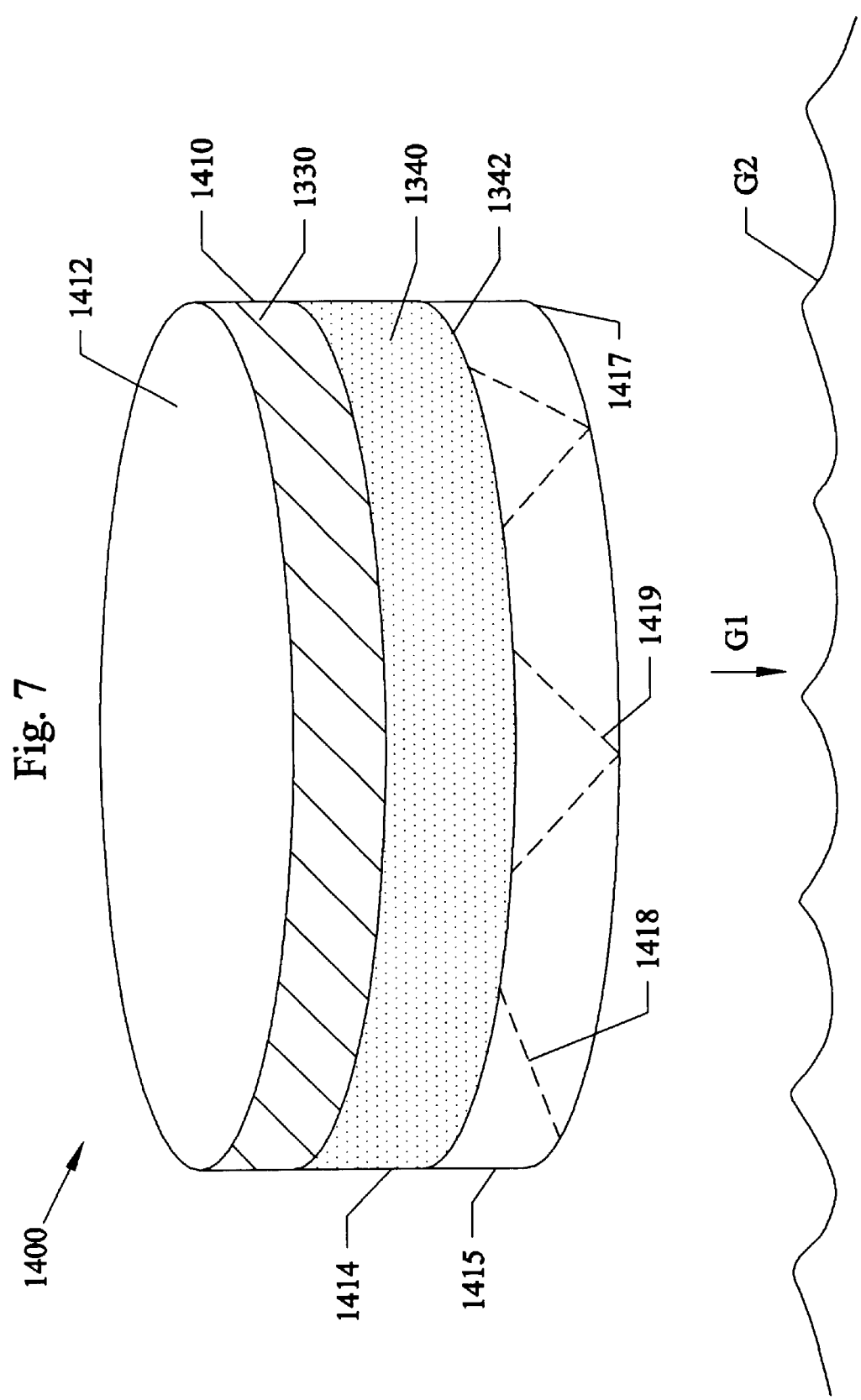
FIG. 7 is a side view of a third preferred ground surface embodiment for an arthropod control application.

FIG. 7 is a side view of a third embodiment 1400 of the invention showing another ground surface application with ground insertion edges. Chamber 1410 can be similar in dimensions to chamber 1310 described in detail in reference to the third embodiment and can include a non-edible foraging matrix 1330 treated with a slow acting non-repellent toxicant inside the chamber 1310 against the upper lid end 1412 with an edible non-toxic food source 1340 underneath the matrix 1330. The chamber 1410 can have a lower extending cylindrical thin side walls 1415, which can extend up to approximately 1 to approximately 5 cm below the non-edible food source layer 1340, so that the bottom edges 1417 can easily be pushed into a ground surface. Although the side walls are shown as being cylindrical with a hollow center, the side walls 1415 can be of different shapes such as but not limited to rectangular, square, triangular, and the like.

Alternatively, the bottom edge can have individual teeth portion(s) 1418 with sharp edges 1419 for aiding in the ground insertion such as triangular shaped, and the like. When used, the embodiment 1400 similar to the seventh embodiment is pushed into the ground in the direction of arrow G1 until the surface of the ground G2 is adjacent to the lower surface 1342 of the edible non-toxic layer 1340. Embodiment 1400 can be used similar to the previous embodiments and can also kill arthropods in a similar manner over time.

Fourth Embodiment

Figure 8:
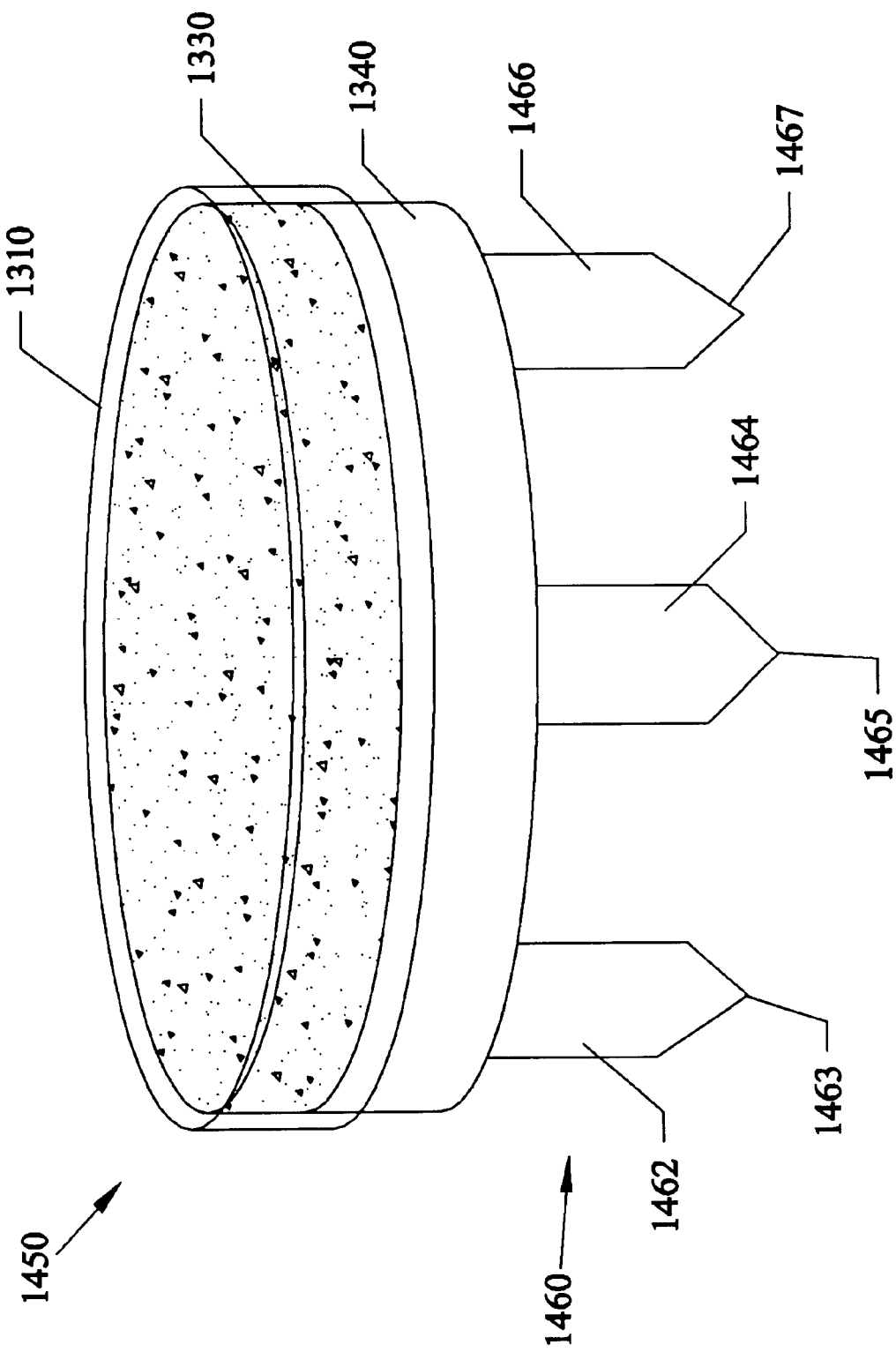
FIG. 8 shows a side view of a fourth ground surface embodiment for ground surface application.

FIG. 8 shows a side view of a fourth embodiment 1450 of the invention showing another ground surface application where the layer of slow acting non-repellant toxicant mixed with the non-edible foraging matrix 1330 is within an open end of chamber 1310, with an edible non-toxic material layer 1340 such as a foam material and the like, and individual mini type stakes 1460 extend out from layer 1340. Each of the mini type stakes 1360 can include a longitudinal member portion 1462, 1464, 1466 and a sharp bottom tip edge 1463, 1465, and 1467. The stakes can be formed from materials such as wood, plastic, and metal, and can be pre-inserted into layer 1340. Alternatively, stakes 1460 can be pre-attached to chamber 1310.

Figure 9:
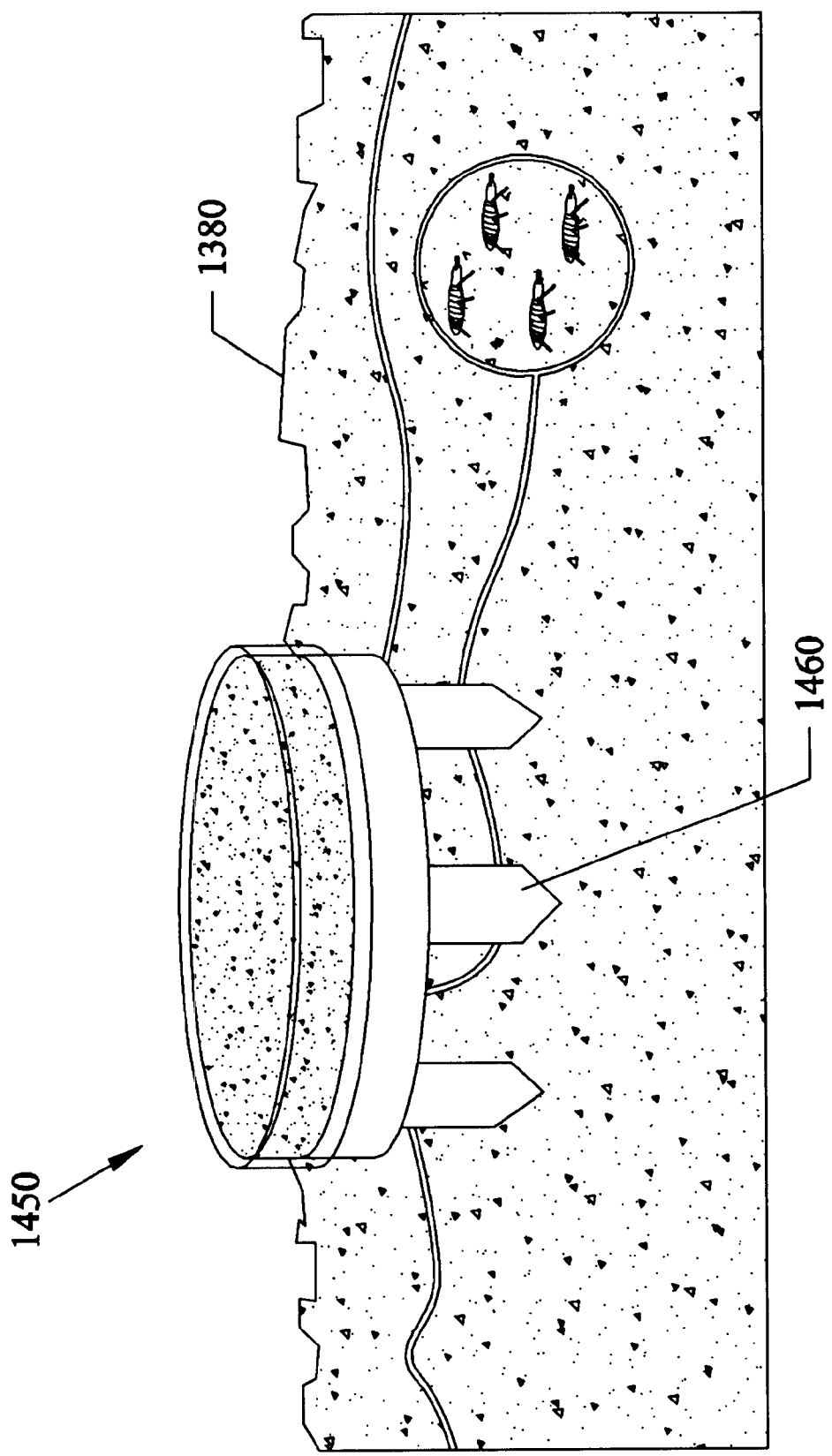
FIG. 9 shows the fourth embodiment of FIG. 8 mounted in the ground surface.

FIG. 9 shows the fourth embodiment 1450 of FIG. 8 mounted in the ground surface 1380. Embodiment 1450 can be used similar to previous embodiments to kill arthropods over time.

Fifth Embodiment

Figure 10:
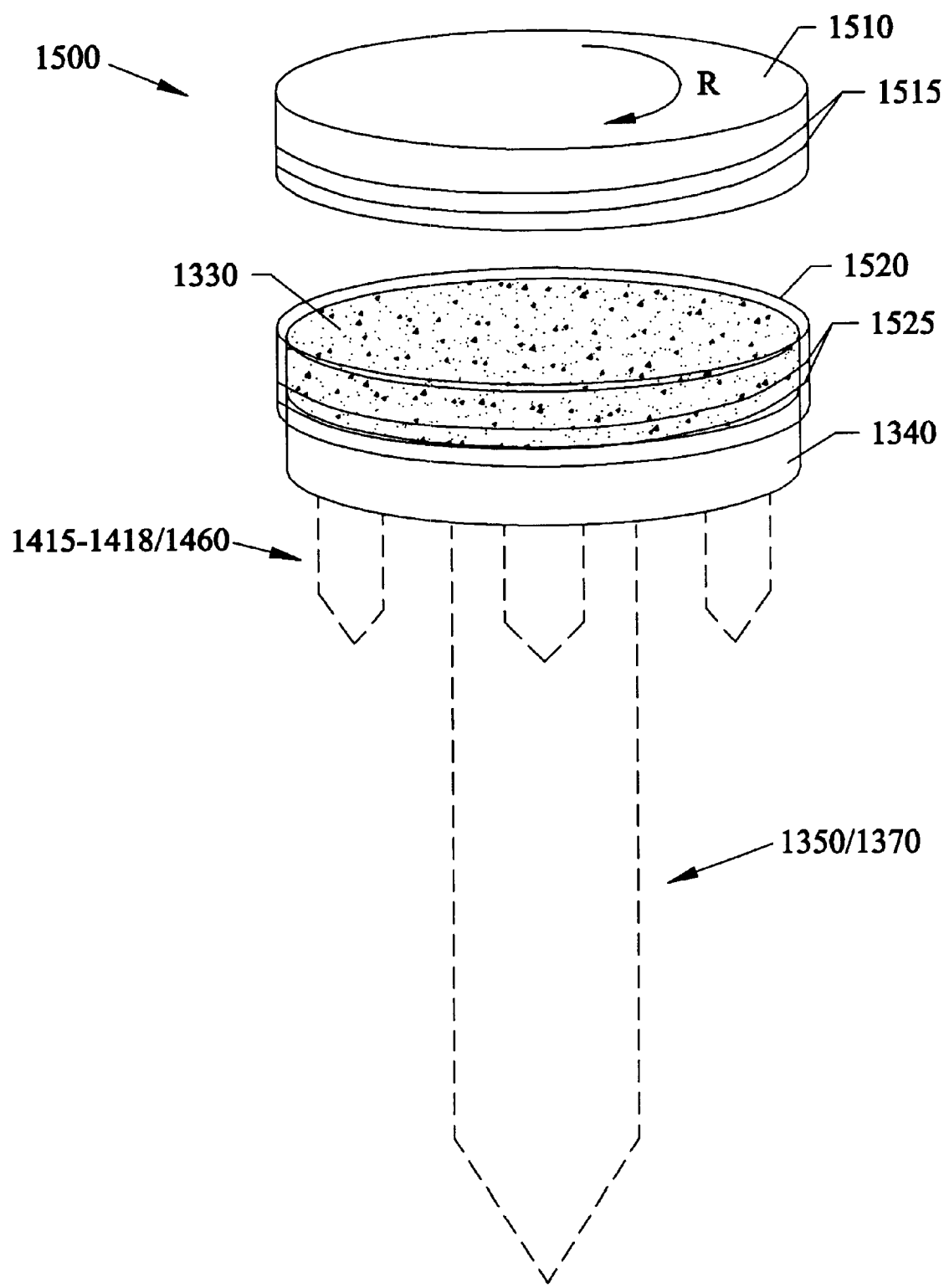
FIG. 10 shows a fifth embodiment for ground surface application with a screw top.

FIG. 10 shows a fifth embodiment 1500 for ground surface application with a screw top 1510, 1520. Components 1330, 1340, 1415–1418, 1460 and 1350, 1370 correspond to those previously described in previous embodiments. Here, the chamber can include two portions, a lid portion 1510 having downwardly extending sides with threaded surfaces 1515, and a lower hollow chamber portion 1520 having threaded sides 1525. Lower chamber portion 1520 can have an upper open end and a lower open end for housing the layers 1330, 1340. The threaded sides allow the lid portion 1510 to mateably screw onto the threads 1525 of the lower chamber portion 1520. For example lid portion 1510 can be attached by rotating in a clockwise direction as shown by arrow R to lower portion 1520, and can be separated by rotating in a counter-clockwise direction. The fifth embodiment 1500 allows for easy access to the interior of the chamber 1510, 1520 to check on the contents without having to physically remove the embodiment from the ground. This embodiment allows for reusability overtime since the interior content layers 1330, 1340 can be replaced without having to physically remove the embodiment from the ground. Any of the stake and ground insertable portions previously described can be used with this embodiment. Embodiment 1500 can also be used similar to the previous embodiments to kill arthropods over time.

Sixth Embodiment

Figure 11:
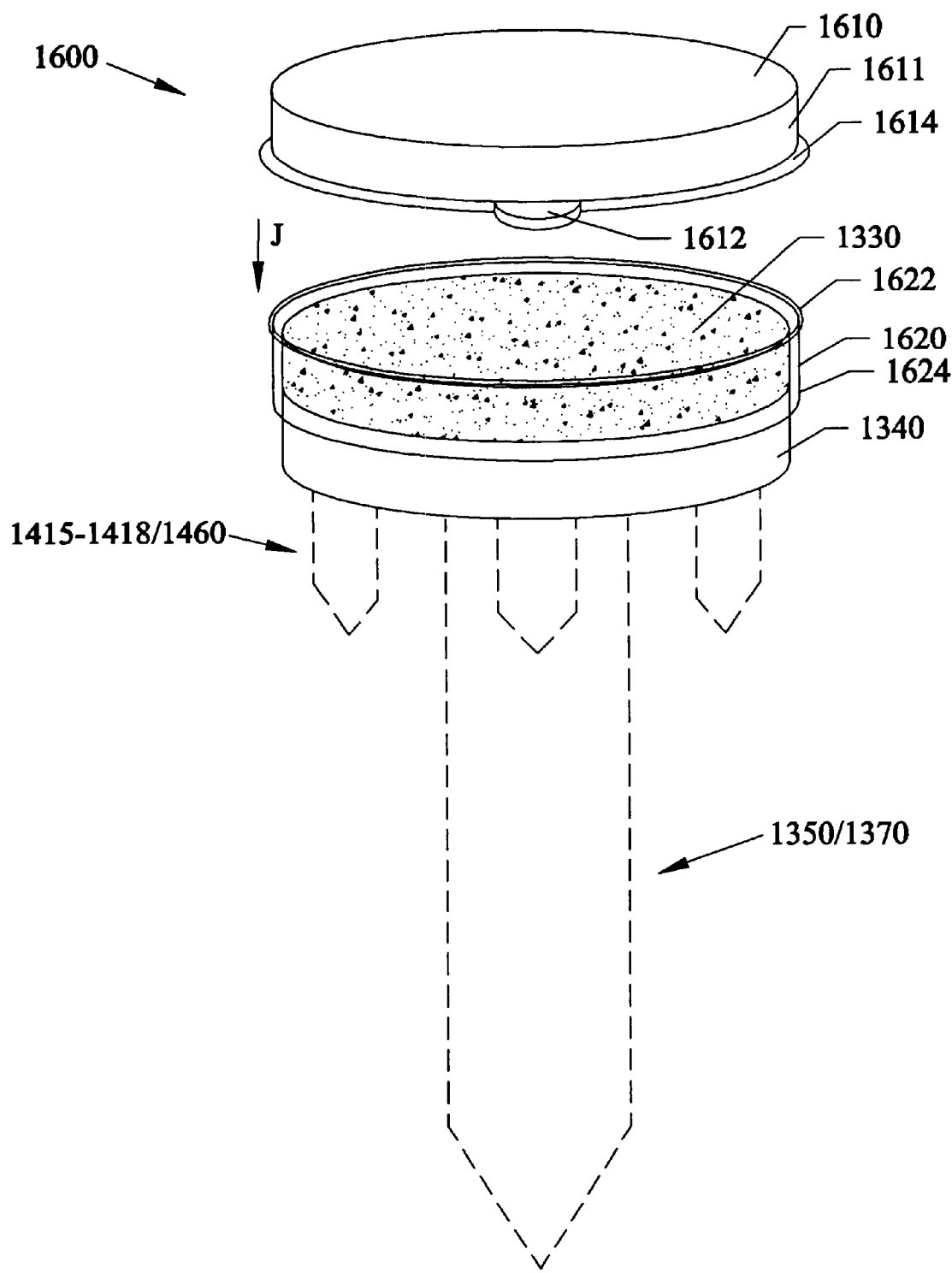
FIG. 11 shows a sixth embodiment for ground surface application with snap top.

FIG. 11 shows a sixth embodiment 1600 for ground surface application with snap top. Components 1330, 1340, 1415–1418, 1460 and 1350, 1370 correspond to those previously described in previous embodiments. Here, the chamber can include two portions, a lid portion 1610 having downwardly extending sides 1611 with ridge edge 1614, and tab 1612, and a lower hollow chamber portion 1620 having sides 1624 with an upper lip edge 1622. Lower chamber portion 1620 can have an upper open end and a lower open end for housing the layers 1330, 1340. The ridge edge 1614 allow the lid portion 1610 to snap onto the raised upper lip edge 1622 of the lower chamber portion 1620. For example lid portion 1610 can be attached by being moved in a downward direction as shown by arrow J to lower portion 1620, and can be separated by being moved in an opposite direction. The sixth embodiment 1600 allows for easy access to the interior of the chamber 1610, 1620 to check on the contents without having to physically remove the embodiment from the ground. This embodiment allows for reusability overtime since the interior content layers 1330, 1340 can be replaced without having to physically remove the embodiment from the ground. Any of the stake and ground insertable portions previously described can be used with this embodiment. Embodiment 1600 can also be used similar to the previous embodiments to kill arthropods over time.

Seventh Embodiment

Figure 12:
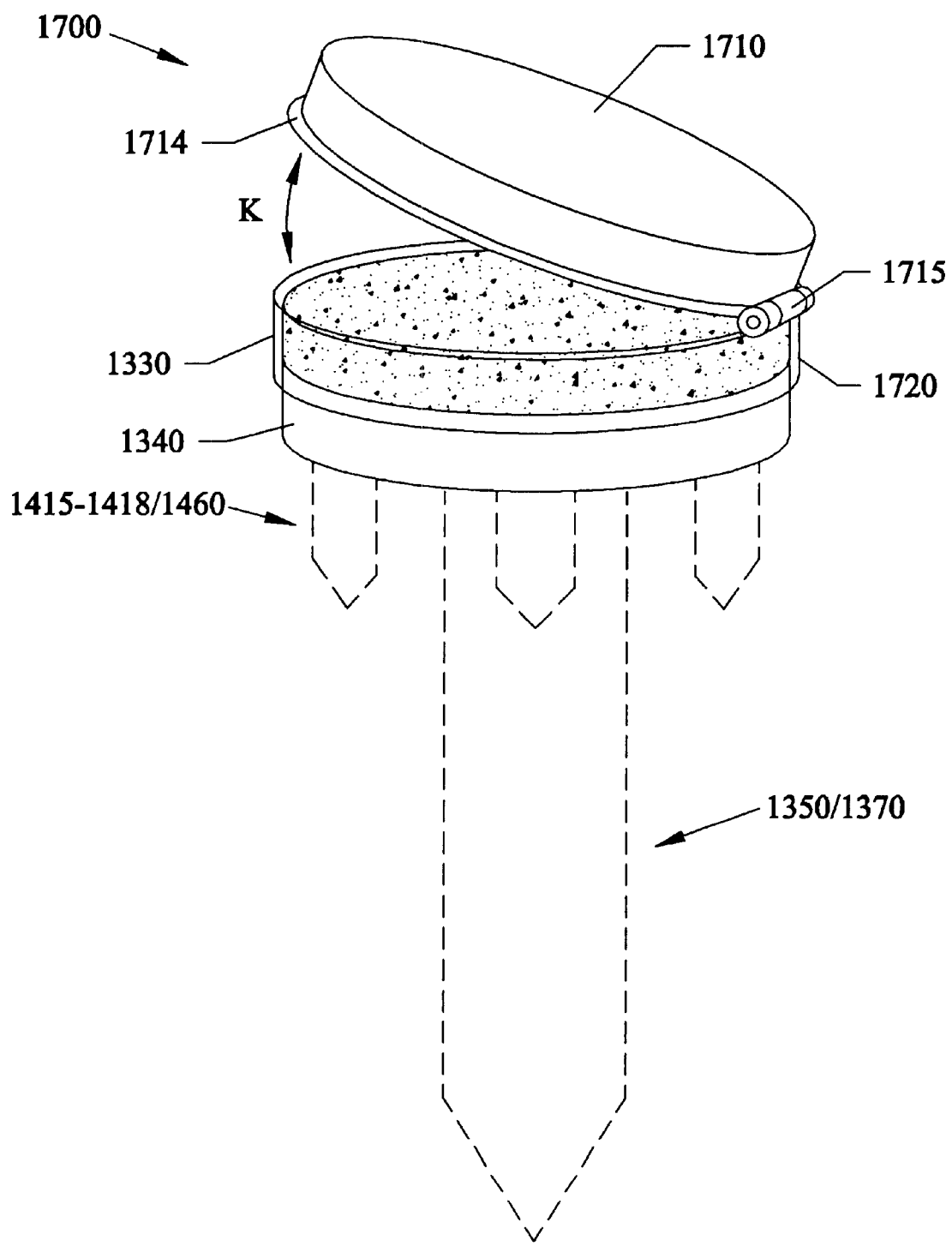
FIG. 12 shows a seventh embodiment for ground surface application with hinge top.

FIG. 12 shows a seventh embodiment 1700 for ground surface application with hinge top. Components 1330, 1340, 1415–1418, 1460 and 1350, 1370 correspond to those previously described in previous embodiments. Here, the chamber can include two portions, a lid portion 1710 having downwardly extending sides with raised bottom edge 1714, and a lower hollow chamber portion 1720. Lower chamber portion 1720 can have an upper open end and a lower open end for housing the layers 1330, 1340. A hinge portion 1715 allows lid portion 1710 to open and close in the direction of double arrow K relative to lower chamber portion 1720. The seventh embodiment 1700 allows for easy access to the interior of the chamber 1710, 1720 to check on the contents without having to physically remove the embodiment from the ground. This embodiment allows for reusability overtime since the interior content layers 1330, 1340 can be replaced without having to physically remove the embodiment from the ground. Any of the stake and ground insertable portions previously described can be used with this embodiment. Embodiment 1700 can be used similar to the previous embodiments to kill arthropods over time.

Figure 13:
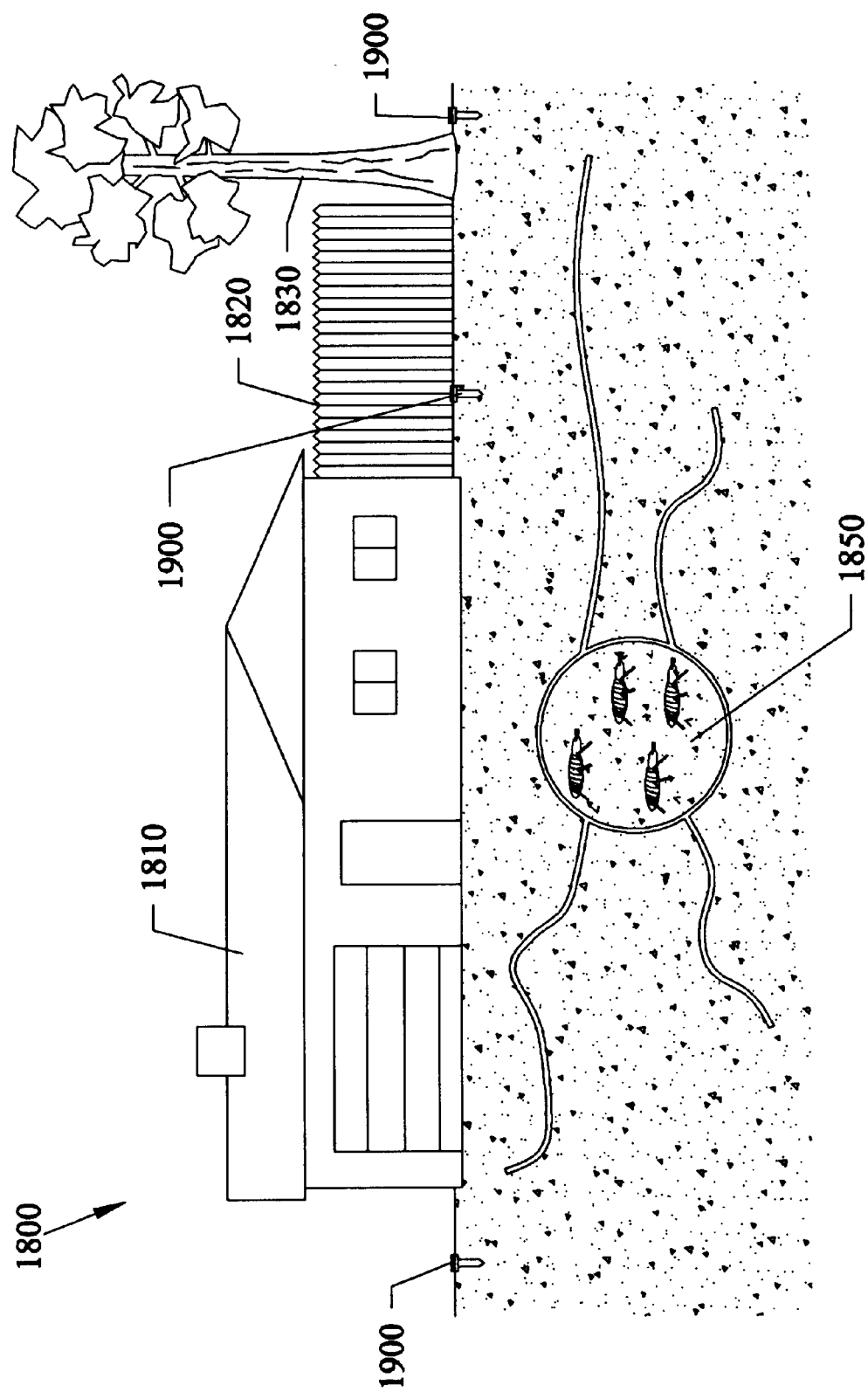
FIG. 13 shows a preferred placement application for the ground surface embodiments previously described.

FIG. 13 shows a preferred placement application for the ground surface embodiments previously described. Label 1900 refers to any of the ground surface embodiments previously described, which can be placed adjacent to any structures such as but not limited to buildings such as homes 1810, wood type fences 1820, trees 1830, and the like, in order to protect them from destructive arthropods 1850.

Additionally, the embodiments can be attached directly to materials themselves, such as but not limited to being attached to landscape timbers including recycled railroad ties, which has been known to transport pest species such as Formosan subterranean termites around the country. For example, the teeth of the embodiments can be used for such an attachment.

Although, the preferred embodiments refer to the stake being an edible material such as wood, the stake can be made of other edible materials such as but not limited to plastic, hardened foam, and the like, and combinations, thereof.

Although the bottom layer 1340 has been referred to as being an edible type material such as foam, the term foam can include but not be limited to various types of foams such as but not limited to open cell foam, closed cell foam, Styrofoam, and the like, and combinations, thereof.

Although some types of non-edible foraging matrix materials were described, other types of non-edible foraging matrix materials can be used, such as but not limited to soil, sand, gravel, rocks, pebbles, shale, expanded shale, clay, and the like, and combinations thereof. Additionally, other non-edible foraging matrix materials can be used such as those that can be ground or fashioned to the particle size that arthropods such as but not limited to termites and other arthropods can pick up and can forage through. Additionally, any other types of non-edible foraging materials that arthropods such as but not limited to termites, can be used such as but not limited to dental cast-stone and other porous materials, and the like, and combinations thereof with any other materials described here.

While various shapes for the embodiments are shown, any of the invention embodiments can include various types of geometrical shapes such as but not limited to rectangular, polygon, disc, global, cylindrical, triangular, and the like, and various combinations thereof, and the like.

Although each of the embodiments is separately described above, each and every feature of the embodiments can be interchanged and used with any of the other embodiments. Likewise, each of the embodiments can be used in different combinations with each other.

In addition to the slow-acting non-repellent toxicants previously described, other slow-acting toxicants can also be used such as those listed but not limited to those in

TABLE 2

Additional Slow-Acting Toxicants

| TYPE | SLOW-ACTING TOXICANTS |
| --- | --- |
| Non-repellants: | Chlorfenapyr, Imidacloprid, Friponil |
| Bait Materials: | Hydramethylnon, Sulfluramid, Hexaflumuron |
| IGRs: | Pyriproxyfen, methoprene and lufenuron, dimilin |
| Others: | Chlorpyrifos, and their active derivatives |
| Botanicals: | Neem (azadiractin) |
| Inorganics: | Boric acid based. |

Although the layer in the chamber adjacent to the arthropod entry is described as being an edible non-toxic food source, the layer can also be an arthropod attractant material that arthropods do not necessarily eat, but are attracted to such as pseudo-scents, and the like.

While the preferred embodiments have been described as being used adjacent to structures such as manmade structures such as wood-containing houses, wood-containing buildings, wood-containing sheds and wood-containing fences, and the like, and combinations thereof, the invention embodiments can be placed adjacent to other non-manmade items that can be damaged by arthropods, such as but not limited to plants, shrubbery, gardens, and the like, and combinations thereof. Likewise the invention embodiments can be placed adjacent to both manmade and natural items that can be damaged by the arthropods.

Although some of the preferred embodiments have been described as being specifically used with subterranean type termites, the invention embodiments are applicable to other types of crawling arthropods, such as but not limited to termites, carpenter ants, fire ants, roaches, and the like, and combinations, thereof, and the like.

Although the invention embodiments are described as being used primarily with crawling type arthropods, the invention can be used with other types of arthropods such as above ground termites, and the like., and in combinations thereof with other non-crawling arthropods. Additionally, the invention embodiments can be used in combination treatments for both crawling and non-crawling arthropods, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A ground surface treatment method of killing arthropods, comprising the steps of:
   (a) providing a chamber with at least one open end, the chamber having at least one layer of a nontoxic food source with one side adjacent to the one open end being accessible to arthropods;
   (b) inserting a mixture of a foraging non-edible matrix mixed with a slow-acting and non-repellent toxicant into the chamber adjacent to a second side of the one layer of the nontoxic food source;
   (c) positioning the at least one open end of the chamber adjacent to a ground surface, wherein arthropods enter into the at least one open end of the chamber to eat through the non-toxic food source into the toxicant treated non-edible matrix, so that slow-acting and non-repellent toxicant destroys arthropods in their colonies over time.

2. The ground surface treatment method of claim 1, further comprising the step of: placing the chamber adjacent to a colony of arthropods.

3. The ground surface treatment method of claim 2, wherein the arthropods include at least one of: termites, carpenter ants, fire ants, and roaches.

4. The ground surface treatment method of claim 1, further comprising the step of: placing the chamber adjacent to a manmade structure, the structure selected from at least one of: a building, a house, a fence, a shed, and combinations thereof.

5. The ground surface treatment method of claim 1, further comprising the step of: placing the chamber adjacent to at least one of: a tree, a plant, a garden and a shrub.

6. The ground surface treatment method of claim 1, further comprising the step of: attaching the chamber to a ground insertable member, which when inserted into the ground allows the edible layer in the chamber to be adjacent to the ground surface.

7. The ground surface treatment method of claim 6, wherein the ground insertable member includes: a non-toxic edible material.

8. The ground surface-treatment method of claim 7, wherein the ground insertable member includes: a wood containing stake.

9. The ground surface treatment method of claim 1, further comprising the step of: providing the chamber with a window portion for allowing a portion of interior contents of the chamber to be seen from outside the chamber.

10. The ground surface treatment method of claim 1, further comprising the step of: replacing a portion of the interior contents of the chamber so that the chamber is reusable over time.

11. The ground surface treatment method of claim 1, wherein the nontoxic food source includes the step of:
   placing a nontoxic food source selected from at least one of: wood, paper, cellulose material, foam, plastic, and mixtures thereof, into the open end of the chamber.

12. The ground surface treatment method of claim 1, wherein the step of inserting the foraging non-edible matrix mixed with the slow-acting and non-repellent toxicant includes the step of:

mixing the slow-acting and non-repellent toxicant with the foraging non-edible matrix selected from at least one of: soil, gravel, rocks, pebbles, shale, and mixtures thereof.

13. The ground surface treatment method of claim 1, wherein the chamber includes the step of:
   selecting a shape from at least one of: a disc, a cylinder, a rectangle, a triangle, a polygon, and combinations thereof.

14. A ground surface apparatus for killing arthropods, comprising in combination:
   a chamber having at least one opening with a layer formed from a non-toxic, edible arthropod food source;
   a mixture of a foraging non-edible foraging matrix mixed with a slow-acting and non-repellent toxicant the mixture being within the chamber on an opposite side of the non-toxic edible layer; and
   a ground surface adjacent to the at least one opening for allowing arthropods to enter into and pass out of the chamber to disperse the slow acting and non-repellent toxicant to their colony to kill arthropods over time.

15. The ground surface apparatus of claim 14, further comprising:
   a manmade structure that is being protected from the arthropods, the structure selected from at least one of: a house, a building, a shed, a fence, and combinations thereof.

16. The ground surface apparatus of claim 14, further comprising: a natural item that is being protected from the arthropods.

17. The ground surface apparatus of claim 16, wherein the natural item is selected from at least one of: a tree, a plant, a shrubbery, a garden, and combinations thereof.

18. The ground surface apparatus of claim 14, further comprising: a ground insertable member attached to the chamber, which when inserted into the ground allows the edible layer in the chamber to be adjacent to the ground surface.

19. The ground surface apparatus of claim 18, wherein the ground insertable member includes: a non-toxic edible material.

20. The ground surface apparatus of claim 19, wherein the ground insertable member includes: a wood containing stake.

21. The ground surface apparatus of claim 14, further comprising:
   a window portion on the chamber for allowing a portion of interior contents of the chamber to be seen from outside the chamber.

22. The ground surface apparatus of claim 14, further comprising:
   means for allowing an interior content of the chamber to be replaced so that the chamber is reusable over time.

23. The ground surface apparatus of claim 22, wherein the replacement means includes: a cap portion having a snap edge so that the cap portion can be completely separated from the chamber.

24. The ground surface apparatus of claim 22, wherein the replacement means includes: a cap portion having a hinge so that the cap portion can be hingedly attached to the chamber.

25. The ground surface apparatus of claim 22, wherein the replacement means includes: a cap portion having threads for allowing the cap portion to rotatably screw onto the chamber.

26. The ground surface apparatus of claim 14, wherein the nontoxic food source is selected from at least one of: wood, paper, cellulose material, foam, plastic, and mixtures thereof.

27. The ground surface apparatus of claim 14, wherein the foraging non-edible matrix is selected from at least one of: soil, gravel, rocks, pebbles, shale, and mixtures thereof.

28. The ground surface apparatus of claim 14, wherein the chamber includes a shape selected from at least one of: a disc, a cylinder, a rectangle, a triangle, a polygon, and combinations thereof.

29. The ground surface apparatus of claim 14, wherein the ground insertable member includes: one stake.

30. The ground surface apparatus of claim 14, wherein the ground insertable member includes: two stakes adjacent to one another having at least one narrow groove therebetween for allowing arthropods to pass along the groove.

31. The ground surface apparatus of claim 14, wherein the ground insertable member includes: plural teeth members.

32. The ground surface apparatus of claim 14, wherein the ground insertable member includes: plural stakes separated apart from one another.

33. A ground surface composition for dispersing slow acting non-repellant toxicants to arthropods comprising:
   a non-edible foraging matrix;
   a slow acting, non-repellant toxicant mixed with the matrix to form a mixture; and
   an edible layer adjacent the mixture placed between the mixture and a ground surface for allowing arthropods to access the mixture.

34. The ground surface composition of claim 33, wherein the non-edible foraging matrix is selected from at least one of: soil, gravel, rocks, pebbles, shale, and mixtures thereof.

* * * * *